(12) United States Patent
Trani et al.

(10) Patent No.: US 7,890,354 B2
(45) Date of Patent: Feb. 15, 2011

(54) SYSTEMS AND METHODS FOR LONG-TERM CARE INSURANCE WITH IMMEDIATE AND ONGOING HEALTH CARE MAINTENANCE BENEFITS

(75) Inventors: Louis M. Trani, Salt Lake City, UT (US); Earl Roderick Ross, Salt Lake City, UT (US)

(73) Assignee: Equitable Life and Casualty Insurance, Salt Lake City, UT (US)

( * ) Notice: Subject to any disclaimer, the term of this patent is extended or adjusted under 35 U.S.C. 154(b) by 204 days.

(21) Appl. No.: 11/035,475

(22) Filed: Jan. 14, 2005

(65) Prior Publication Data

US 2006/0161461 A1   Jul. 20, 2006

(51) Int. Cl.
   *G06Q 40/00* (2006.01)
(52) U.S. Cl. .............................. 705/4; 705/3
(58) Field of Classification Search ............ 705/1, 705/36 R, 36, 38, 39, 2–4; 706/45, 46; 434/127, 434/262, 185, 236; 600/300, 425; 707/100, 707/9
   See application file for complete search history.

(56) References Cited

U.S. PATENT DOCUMENTS

| | | | |
|---|---|---|---|
| 5,517,405 A | 5/1996 | McAndrew et al. | |
| 5,937,387 A * | 8/1999 | Summerell et al. | 705/2 |
| 6,014,632 A | 1/2000 | Gamble et al. | |
| 6,067,522 A | 5/2000 | Warady et al. | |
| 6,076,072 A * | 6/2000 | Libman | 705/36 R |
| 6,078,890 A | 6/2000 | Mangin et al. | |
| 6,092,047 A | 7/2000 | Hyman et al. | |
| 6,102,706 A | 8/2000 | Khoo et al. | |
| 6,482,156 B2 | 11/2002 | Iliff | |
| 6,584,446 B1 * | 6/2003 | Buchanan et al. | 705/4 |
| 6,684,190 B1 | 1/2004 | Powers et al. | |
| 2002/0010597 A1 * | 1/2002 | Mayer et al. | 705/2 |
| 2002/0032580 A1 * | 3/2002 | Hopkins | 705/2 |
| 2002/0049617 A1 * | 4/2002 | Lencki et al. | 705/4 |
| 2002/0103678 A1 * | 8/2002 | Burkhalter et al. | 705/4 |
| 2002/0152097 A1 | 10/2002 | Javors | |
| 2002/0184057 A1 * | 12/2002 | Hayashi et al. | 705/4 |
| 2003/0009355 A1 * | 1/2003 | Gupta | 705/2 |
| 2003/0022141 A1 | 1/2003 | Packard | |
| 2003/0187693 A1 * | 10/2003 | Oka et al. | 705/2 |
| 2003/0191669 A1 | 10/2003 | Fitzgerald et al. | |

(Continued)

OTHER PUBLICATIONS

American Independent Underwriters Glossary web page . . . [Retrieved from Internet Jan. 1, 2009]. URL: <http://www.aim-aiu.com/glossary.htm#L>.*

(Continued)

*Primary Examiner*—Gerald J. O'Connor
*Assistant Examiner*—Natalie A Pass
(74) *Attorney, Agent, or Firm*—TraskBritt, P.C.

(57) ABSTRACT

Methods and systems related to long-term care insurance. Long-term care insurance policies are priced by stratifying potential purchasers according to risk factors which are explored during the underwriting process. In addition to coverage for long-term care, immediate health care benefits are provided to the purchasers in the form of an interactive health management program. The health management program may include contact between health care advisors and the availability of a wide range of health care services to provide positive health planning and resources to the policyholders. Underwriting and portions of the health management program may be provided through automation to reduce overhead expenses.

20 Claims, 3 Drawing Sheets

U.S. PATENT DOCUMENTS

2003/0229522 A1 12/2003 Thompson et al.
2004/0143446 A1 7/2004 Lawrence
2004/0176982 A1 9/2004 Kilgore et al.
2005/0288968 A1* 12/2005 Collins .......................... 705/4
2006/0218010 A1* 9/2006 Michon et al. ................. 705/3

OTHER PUBLICATIONS

MedicineNet Definition web page. [Retrieved from Internet Jan. 1, 2009]. URL: <http://www.medterms.com/script/main/art.asp?articlekey=24267&pf=3&page=1>.*

Pannone, Pat, Disease Management Comes to Long Term Care, Advisor, May/Jun. 2000, pp. 6-7.

Secured Independence, Inc. Launches Program to Reduce Disability and Claims Costs for LTC Insurance Policyholders, Secured Independence, Inc., Partners in Successful Aging.

Ware, SF-36 Health Survey Update, SPINE, 2000, pp. 3130-3139, vol. 25, No. 24.

Get Palliative Care.org (visited Sep. 8, 2008) <http://www.getpalliativecare.org/whatis>.

Disability Insurance (visited Aug. 11, 2008) <http://www.investorguide.com/printarticle.cgi?ref=336>.

3HC Compassionate care is our calling™ Hospice Admission Criteria, <http://www.3hc.org/clinrespgs%5CAdmissionCriteria.html>, visited Jun. 19, 2009.

Criteria for Hospice Admission, <http://organizedwisdom.com/Criteria_for_Hospice_Admission>, visited Jun. 19, 2009.

Hospice of Virginia, <http://www.hospiceva.com/physician/guidelines/default.aspx>, visited Jun. 19, 2009.

LifePath Hospice, <http://www.lifepath-hospice.org/professionals/admission.html>, visited Jun. 19, 2009.

National Clearinghouse for Long-Term Care Information, U.S. Department of Health and Human Services, website (last modified Oct. 22, 2008).

Medicare.gov, The Official U.S. Government Site for Medicare, website (last updated Mar. 25, 2009).

Long-term care, Wikipedia available at http://en.wikipedia.org/wiki/Long-term_care (last modified on Jul. 18, 2010).

* cited by examiner

SYSTEMS AND METHODS FOR LONG-TERM CARE INSURANCE WITH IMMEDIATE AND ONGOING HEALTH CARE MAINTENANCE BENEFITS

TECHNICAL FIELD

The present invention relates generally to systems and methods for providing and underwriting long-term care insurance. More particularly, the present invention relates to systems and methods for providing and underwriting long-term care insurance that provides immediate benefits to purchasers in addition to the long-term care benefits.

BACKGROUND

One of the biggest and most important demographic changes facing the United States is the aging population. Both the number and proportion of older people are increasing. In 2000, 35 million Americans were age 65 and older, representing 12.4 percent of the total population. This older population is expected to reach 54 million in 2020 and more than double in size by 2050, to account for 20 percent of our population.

Long-term care insurance policies were first offered to the public by insurance companies at about the time when Medicare came into being in 1966. These first policies were developed when almost everyone confined to a nursing home was elderly and unable to take care of themselves because of chronic cognitive or physical impairments. That is, their health conditions had deteriorated to the point that they were no longer able to take care of themselves without the assistance of another person. They were not expected to recover from these conditions. Other forms of long-term care, such as home health care provided in a patient's home or extended recovery care provided in a specialized facility were virtually non-existent.

As a result, the first long-term care insurance policies covered only nursing home care. Pricing the policies was difficult because there was very little data available to assist insurers. Thus, most policies provided fixed benefits without regard to patients' actual health conditions, that is, their medical, physical, and mental states of health.

Today, almost half of all senior patients need skilled medical care that cannot be provided by friends or family during their recovery after release from a hospital. Technological advances now allow most care provided in a nursing home to be provided in patients' homes. Thus, whether patients recover in a nursing home or in their own home now depends more often on the type of care they can afford. Because home health care for recuperating patients is frequently more expensive than nursing home care, and because the combination of Medicare and private Medigap insurance policies (which cover amounts not paid by Medicare) can pay 100% of the costs for nursing home care during the first one hundred days, most recuperating patients are sent to nursing homes even though 75% to 80% strongly prefer to recover at home.

While long-term care policies are now available that include benefits for home health care, these policies are subject to similar shortcomings in the rate of sales as the original long-term care policies. It is estimated that only about 2% of people age 50 and older are covered by long-term care policies even though long-term care represents the largest potentially devastating financial risk for most seniors. In an article in the May 1996 Best's Review Life/Health Ed. by Ron Panko, who cited Steven Devlin, Ph. D. Associate Director of the Boettner Center of Financial Gerontology at the Univ. of Pa., reporting on a study of 5,800 families nationwide showing that in the last six months of their parents' lives, 31% of the families spent all of their life savings on their parents. "That's frightening for families," he says. "You may be 70 and your mother is 90, and you are spending all of your money caring for her."

Often, the reason for not purchasing long-term health care policies comes down to the perceived lack of benefit to the potential purchaser at the time the policy may be purchased for reasonable amounts. As potential purchaser in their 40's or 50's weighs the potential benefits of obtaining a long-term care policy, which may be needed twenty, thirty, or forty years in the future, against the current costs, the possibility of need may appear too remote. As these potential purchasers weigh the perceived "remote" benefits against alternative current uses for the same funds, the choice is often against purchasing this insurance. Instead, these policies are most often purchased by those in their mid-60's at higher rates, or are never purchased at all. As the demographic shift to an older population occurs, the strain on society from needed but unfunded long-term care for seniors increases. Methods that result in the purchase of long-term health care policies would thus be an improvement in the art.

Also known in the art are attempts to offer information on health care to the public at large, such as public awareness campaigns on various diseases or conditions. Similarly, health information programs have been provided by hospitals and other health care entities as additional ancillary services to benefit their communities. Typically, this has involved offering services to individuals through providing "health fairs" that are open to the public and provide information on specific issues, such as cardiovascular health or women's health issues. Occasionally, providers have offered services such as "Ask-A-Nurse" call centers, which provide general answers to specific questions from members of the community. However, such programs do not offer specific information that responds to an individual's needs over time and tracks the individual's condition to provide the most needed items. A focused health management program that is individually tailored to specific individuals and provides a variety of services for each individual would be an improvement in the art. Such a method or system that also provides benefits for long-term health care would similarly constitute an improvement in the art.

SUMMARY

The present invention includes methods and systems related to long-term care insurance. Long-term care insurance policies are priced by stratifying potential purchasers according to risk factors which are explored during the underwriting process. In addition to coverage for long-term care, immediate health care benefits are provided to the purchasers in the form of an interactive health management program. The health management program may include contact between health care advisors and the availability of a wide range of health care services to provide positive health planning and resources to the policyholders.

DESCRIPTION OF THE DRAWINGS

It will be appreciated by those of ordinary skill in the art that the various drawings are for illustrative purposes only. The nature of the present invention, as well as other embodiments of the present invention, may be more clearly understood by reference to the following detailed description of the invention, to the appended claims, and to the several drawings.

DETAILED DESCRIPTION

The present invention relates to systems and methods for providing and marketing long-term care insurance policies that provide health management benefits to policyholders prior to the need for utilization of the benefit for long-term health care. It will be appreciated by those skilled in the art that the embodiments herein described, while illustrating certain embodiments, are not intended to so limit the invention or the scope of the appended claims. Those skilled in the art will also understand that various combinations or modifications of the embodiments presented herein can be made without departing from the scope of the invention. For example, it will be appreciated that the methods and systems discussed herein, while particularly suited for providing a specific type of long-term health care policy may be easily adapted into insurance policies that provide additional health care benefits, or may be integrated into life insurance policies. The methods for management of the policies and for providing services to policyholders may also be useful in settings in which provision of services is desired, without the provision of long-term health care benefits. All such alternate embodiments are within the scope of the present invention.

Figure 1:
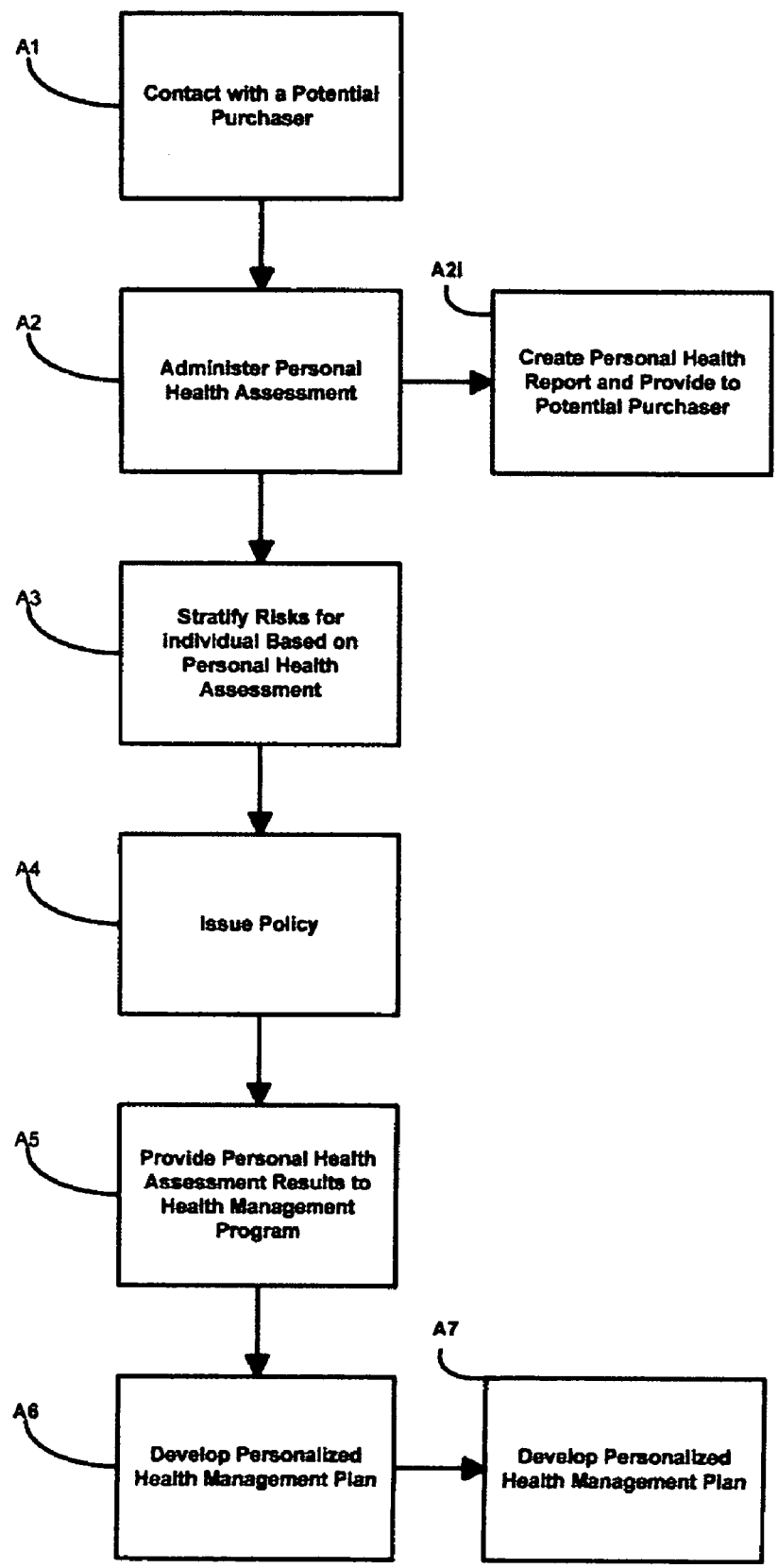
FIG. 1 depicts a flowchart of one illustrative embodiment of a process for collecting initial health assessment information from a potential purchaser, conducting the underwriting process and providing immediate benefits under a policy, in accordance with the principles of the present invention.

Turning to FIG. 1, a flowchart is depicted that illustrates one system or method for collecting and processing information for the underwriting and provision of a long-term health insurance policy and for the design and initiation of a personalized health management program. As depicted in box A1, contact is made with a potential purchaser. This contact may occur in any suitable fashion. For example, an insurance agent who sells a variety of insurance policies may contact existing or potential customers regarding the availability of such a policy. Alternatively, individuals interested in health care insurance or long-term care insurance may contact insurance agencies or companies for information on the available policies. This contact may occur in a traditional manner or may be conducted over a computer connection, such as the internet. Information concerning the available policies may then be provided to potential purchasers. For example, different policies for long-term health care with immediate health management benefits may be offered, which vary in the specific benefits offered (such as total payout amount or the ancillary benefits offered under a health-management program) and correspondingly vary in price.

Once contact between a potential customer and a policy issuing corporation or an insurance agent has been made, and the potential customer desires to apply for a particular long-term health insurance policy with immediate health-management benefits (or to submit an application for several such policies to determine eligibility and specific pricing for each), a personal health assessment is administered to the potential purchaser, as illustrated by box A2. The personal health assessment is designed to elicit information regarding the individual's general health, energy/fatigue, emotional well-being, social functioning, pain, physical and emotional functioning, and possible role limitations due to physical and/or emotional problems. The personal health assessment may be administered by the insurance agent potentially providing the policy to the purchaser as an interview following a specific set of instructions or may be administered by a health counselor or other health care personnel trained in the collection of health care data. In some embodiments, the personal health assessment may include a physical or other exam performed by a physician or other appropriate personnel. The personal health assessment may be a survey, such as the SF-36v2® health survey available from Quality Metric, Inc., which is the recognized standard for patient-reported health outcome assessments to measure general health-related quality of life. Alternatively, specialized assessment tools developed from commercially available tools, such as the SF-36v2® health survey may be used. The SF-36v2® health survey is hereby incorporated by reference herein in its entirety. Other available instruments may be used, and such instruments that provide scores that can be measured against known averages from the general population, or of desirable subpopulations, such as specific age, gender or other classifiable health issue related groupings, (such as the SF-36v2® health survey) are desirable.

As illustrated in box A2i, a personal health report may be generated from the results of the personal health assessment, which provides information on predicted health issues and potential expected health outcomes of the potential purchaser. A copy of the personal health report may be provided the purchaser. The personal health report may be a wellness assessment. The personal health report may be compiled by the person administering the test, or may be compiled by a computer system following commands contained in software, to automatically generate the report, especially where the personal health assessment is administered by computer. The personal health assessment may be performed by comparing the results of the personal health assessment to known averages for the relevant population to which the potential insured belongs (for example, men aged 40 to 45). The personal health report may be provided to all potential purchasers, including those who opt not to purchase long-term care policies and those for whom such coverage is declined by the insurer.

The results of the personal health assessment may be used to stratify the risk associated with the individual during the underwriting process as illustrated in box A3. Underwriting to quantify the risk associated with any particular individual may be conducted in any appropriate manner known to those of ordinary skill in the art. For example. Stratification may follow generally accepted accounting and actuarial principles, using actuarial data obtained from a variety of sources. Automated stratification and underwriting techniques made be used. Examples of such automated techniques include those disclosed in U.S. Pat. No. 6,014,632 to Gamble et al., titled Apparatus and Method for Determining Insurance Benefit Amounts Based on Groupings of Long-Term Care Patients with Common Characteristics, and in U.S. Pat. No. 6,584,446 to Buchanan et al., titled System for Underwriting a Combined Joint Life and Long Term Care Insurance Policy Which is Actuarially Responsive to Long Term Care Demands and Life Expectancies of the Individual Insureds, the contents of each of which are hereby incorporated by reference herein in their entireties.

As part of the underwriting process, each potential insured will be assigned to a stratified risk case, and rate information specific to the benefits desired and that risk class is generated.

This information may then be provided to the potential purchaser. A policy may then be issued to the purchaser, as shown by box A4. The policy may be become effective on the receipt of the first payment by the insurer, and continue its effectiveness through the payment period, which may be for the life of the policy or for a set term.

Once the policy is issued, the insured will be able to access the Health Management Program ("HMP") available as a benefit under the policy. To initiate this process, the results of the personal health assessment are provided to the Health Management Program, as illustrated by box A5. The provision of the results of the personal health assessment may occur in any suitable manner known to those of skill in the art. For example, where the personal health assessment is an interview administered by an insurance agent or and interview and/or examination by a health care professional, the record of the assessment may be sent to the HMP as a document in paper form, in a computer readable format contained on computer readable media, or as a data transmission over a network system or phone line. Alternatively, where the personal health assessment is provided as a computer-based assessment, the results may be automatically routed to the HMP as a data transmission which is accessed after the issuance of a policy. In any event, it is currently preferred that the communication of the data complies with the relevant legal standards governing the privacy of health care information, including HIPAA (the Health Insurance Portability and Accountability Act of 1996).

Upon receipt of the personal health assessment, the HMP develops a personalized health management plan for the individual insured, based upon the results of the personal health assessment, as shown by box A6. The development of the personalized health management plan will be discussed further herein, in connection with FIG. 2.

After development of the personalized health management plan, contact is made between the HMP and the insured to provide information and begin offering health management services. In accordance with the rules of the HMP, these services then continue to be provided to the insured at least until the utilization of the long-term care benefits under the policy. This is illustrated by box A7, and is discussed further herein.

Figure 2:
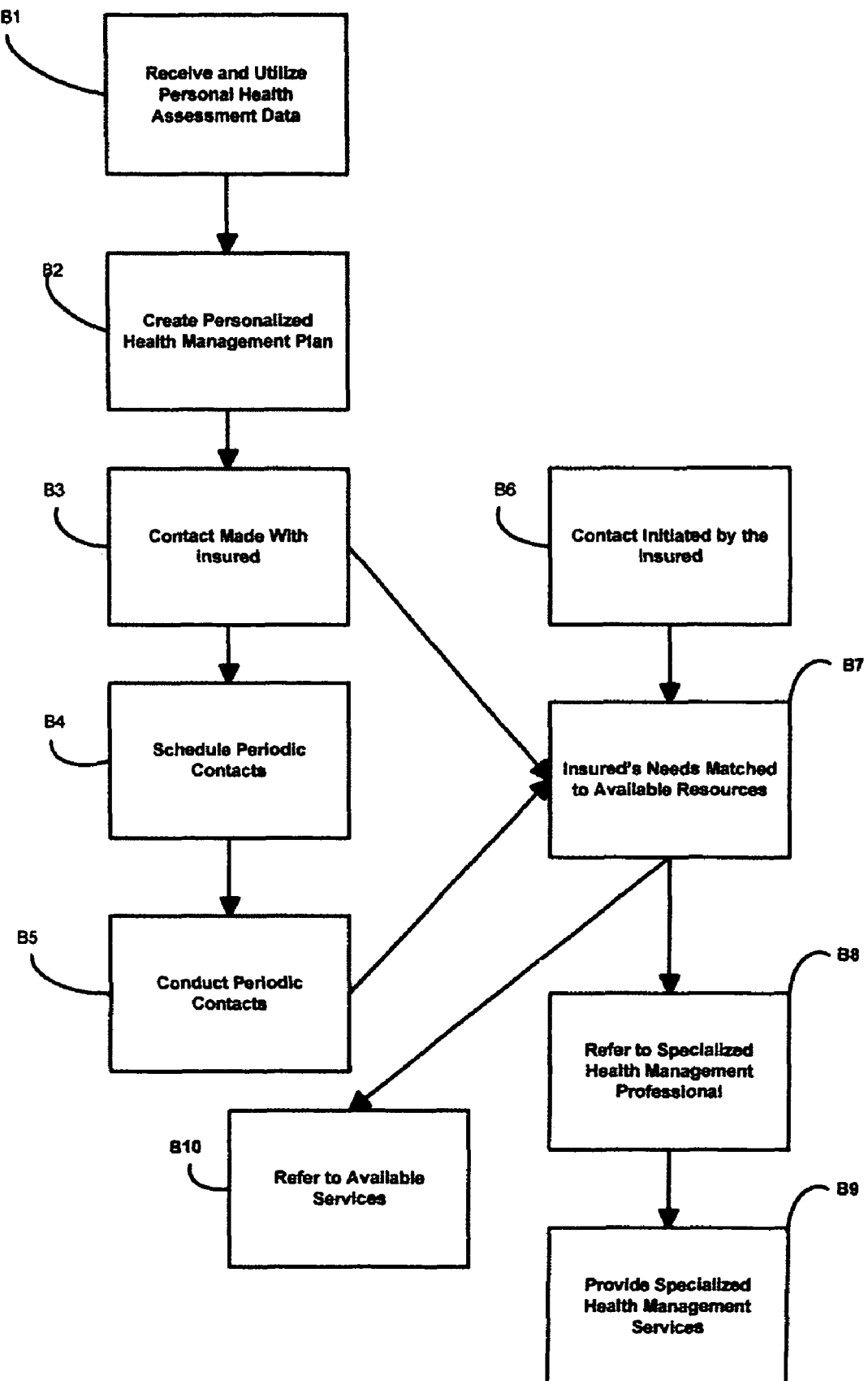
FIG. 2 depicts a flowchart of one illustrative embodiment of a process for providing health management services to a policyholder in accordance with the principles of the present invention.

Turning to FIG. 2, a flowchart illustrating one example of the development and provision of a personalized health management plan to an insured by an HMP in accordance with the present invention is depicted. As depicted in box B1, the process may begin utilizing the data obtained in the personal health assessment obtained during the policy purchasing process. This may begin immediately upon receipt of the data or may begin upon a trigger event, such as a notification that the potential purchaser has purchased a policy and is now eligible to receive benefits. In some embodiments, the insured may initiate this process by informing the HMP of the policy purchase.

As illustrated by box B2, the data received in response to the personal health assessment is then used to create a personalized health management plan for the insured. Depending on the response received, this may require contacting the insured to obtain additional information regarding any particular conditions.

The personalized health management plan will examine a number of health care concerns for individuals, using information that is either provided by the personal health assessment or obtained by contacting the insured based upon initial responses. For example, information may be obtained on whether the insured has a specific medical or physical condition and, if so, the details thereof, or if the insured is at risk for a specific medical or physical condition. Such conditions, and additional specific information a include, for example, arthritis (and the diagnosis, location and treatment thereof), asthma (and the insured's diagnosed breathing function, and treatment, i.e. inhaler, nebulizer, etc.), cancer (or the insured's quantifiable risks thereof and management and treatments therefor); the presence or risks of chronic obstructive pulmonary disease (COPD) (including smoking history, locale/environment, and any treatment, such as bronchodilators, corticosteroids, or oxygen), the presence of risks of heart disease (including cholesterol levels, surgery, and preventative of therapeutic treatments, such as statin drugs) the presence or history of depression or anxiety (including any clinically diagnoses thereof and any treatments received), diabetes (Type I or Type II, control regimens, complications, blood sugar number averages, weight, hypo/hyperglycemia or other pre-diabetic indicators), high blood pressure (regularity of checking, treatments received, including reduction intake of sodium, weight loss if overweight, exercise regularity, smoking cessation, stress reduction, and reduction of caffeine intake), stroke risks (hypertension, TIAs, preventative, treatments, such as weight loss, blood pressure reduction, exercise, stress reduction, smoking cessation), obesity and weight management history, falls/injury history and medical treatments needed, history of or desire for any elective surgeries (including crises or issues and rehabilitation) and diagnosed or risk of osteoporosis (including bone density scan results, use of calcium supplements and weight bearing exercise). It will be appreciated that information and risks for the other health conditions may be explored and integrated into a developed personal health assessment plan.

In developing the personalized health management plan, information obtained from the potential insured in the personal health assessment may be compared to information for the general population (or subpopulation group to which the individual belongs). For example, if the personal assessment generates numerically represented values for a number of different health indicators, these values may be compared to known averages. Those indicators where the individual's values are slightly below the average may be used to select information to be provided during periodic contacts (discussed further herein). For indicators where the individual's value is further away (for example, within 5% of at least one standard deviation from the median or mean, or greater than or equal to standard deviation from the mean), the individual may be classified as "at risk" for associated conditions and more intensive intervention may be designed (such as in-person coaching, repeated follow-ups on those issues over short time periods, such as monthly or weekly contact, or automatic referrals to providers of associated services may be made.)

Contact is then made between the HMP and the insured, as illustrated by box B3. This initial contact is used to inform the insured of the availability of the HMP and the resources available thereunder. At this time, any additional information required or useful for the development of the personalized health management plan may be obtained. This initial contact may be conducted in any suitable form, for example, a telephone call may be made to the insured by HMP personnel, a personal visit or appointment may be conducted, or a computer-based transmission, such as an email may be used. The preferences of the insured provided during the personal health assessment may be used. In some embodiments, the initial contact may be initiated by the insured, at their discretion, to begin the provision of services under the personalized health management plan.

During the initial contact, a schedule of periodic contacts between the HMP and the insured to provide benefits under the personalized health management plan will be established, as illustrated by box B4. These periodic contacts may serve two purposes, first they can allow periodic assessment of the insured's current health concerns, for adjustment of the personalized health management plan over time, as the concerns and condition of the insured vary. Second, the contacts can serve as a periodic reminder to the insured of the availability of the benefits available under from the HMP. The frequency of the periodic contacts may be based upon the data obtained in the assessments (or during contacts) and in response to identified concerns or issues. For example, an insured with few specific identified health concerns may only be scheduled for a periodic contact from the HMP on an initial schedule of every two or three years. As the health concerns of the insured change, for example, if the insured is diagnosed with a chronic health condition or suffers an injury, the schedule is revised to include more frequent contacts (for example, annually or on a quarterly basis). As noted previously herein, should the individual become classified as "at risk" even more intensive intervention may be provided, which will be discussed in connection with FIG. 3.

As shown by box B5, the scheduled periodic contacts are then conducted, providing information to the insured. Of course, it will be appreciated that any insured may have the ability to "opt out" and avoid contacts from the HMP.

As illustrated in box B6, it is currently preferred that the insured be able to initiate contact with the HMP at their discretion. For example, should a health concern arise, the insured may contact the HMP, as by email or telephone or otherwise, to initiate a contact. Depending on the specific health concern, the contact may be conducted over the telephone or by scheduling an appointment for an in-person contact.

For the majority of contacts between the insured and the HMP, it is presently preferred that the contact be conducted by a trained health management coach. Health management coaches may include Registered Nurses or Health Educators trained and supported to provide regular contact with insureds over an extended period. A Health Educator may be a person with a Bachelor's degree, or equivalent experience, in a health education related field, such as Exercise and Sports Science, Community Health Education, Health Promotion, and Nutrition, with specific training in behavioral modification/cognitive coaching techniques.

As illustrated by box B7, during contact between the insured and a coach, whether the initial contact, an insured initiated contact, or a scheduled periodic contact, the coach can help match the insured's needs under the personalized health management plan with resources available under the plan, or with community resources or other services. A referral to such services may then be made, as illustrated by box B10. These services may be specific to the health condition then of concern or in connection with the long-term care benefits, may be aimed at maintaining independence for as long as possible. For example, if the insured has been diagnosed with adult-onset diabetes, the coach may assist the insured in finding a suitable endocrinologist and dietary health care and refer the insured to community support groups. If the insured has been diagnosed with depression, or undergone a recent loss of a loved one, the coach may refer the insured for appropriate counseling or treatment, if available under the plan, or to appropriate community and professional resources. For example, the HMP may offer face to face counseling for relationship issues, emotional struggles or mental illnesses.

Other appropriate services may include referral to legal services, community support services, or the provision of first aid or poison control information. Coaches may also provide education and support to the family members and caregivers of the insured for the purpose of coordinating services and supporting the care available to the insured.

When appropriate, the insured may be referred by a coach to a specialized health management professional at the HMP, as illustrated by box B8. For example, if an insured struggles to reach goals due to significant life problems such as relationship issues, emotional struggles or mental illnesses, the HMP may employ or contract with professional counselors trained in these areas to which the insured may be referred to meet face-to-face and help resolve such hurdles. Other specialists, such as Senior Care Specialists may also be available to insured individuals to help them make decisions regarding care options when their health condition diminishes to the point of needing to access long-term care services. A Senior Care Specialist may have training, such as a degree in a health related field such as Social Work, Nursing, Physical Therapy or Occupational Therapy, specific training in geriatric care management services, or a certification from the National Academy of Professional Geriatric Care Managers as Care Manager Certified (CMC).

A Senior Care Specialist or other specialized health management professional will then provide specialized health management services, including the provision of information and appropriate referrals, as illustrated by box B9. This will be discussed further in connection with FIG. 3. The coach and or specialized health management professional can also provide education and support to the family members and caregivers of the insured for the purpose of coordinating services and supporting the care available to the insured.

Figure 3:
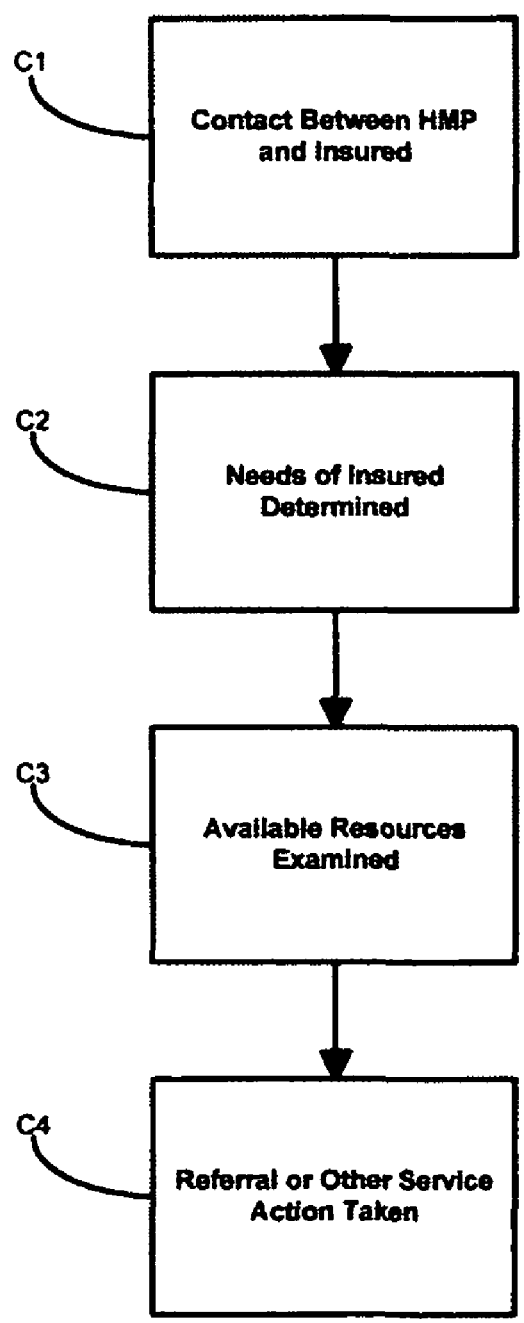
FIG. 3 depicts a flowchart of an illustrative embodiment of a process for providing specialized health care services to a policyholder using a health management system in accordance with the principles of the present invention.

Turning to FIG. 3, a flowchart representing the provision of services by the HMP during a contact between an insured and a coach or specialized health management professional is depicted. As illustrated by box C1, contact occurs between the HMP personnel and the insured. This contact may be initiated by the HMP as the initial contact, as a follow-up contact, or as a part of a scheduled plan of periodic contacts. Alternatively, it may be a contact initiated by an insured, or by a family member of an insured on the behalf of an insured who requires assistance or cannot make such contact on their own.

Once contact is established, the coach or specialized health management personnel determines the needs of the insured, as illustrated by box C2. For an initial or periodic contact, this may be conducted by assessment using the personalized health assessment tool, by conducting a discussion or a series of questions to assess the emotional, physical, functioning, pain, and general health status of the insured. The level of urgency and an identification of any new chronic conditions may be conducted. This information may either be used to update and revise the personal health management plan. When a chronic condition is noted, the coach should obtain the following information, regardless of the specific condition: the history; how and when the condition was diagnosed; the insured's treatment compliance; if there are any treatment medications; and the diet, exercise and associated diagnosis of the insured. A request for authorization or permission to contact the insured's treatment team may also be made. All this information may then be gathered and used to update the personal health management plan and determine the current health management needs of the insured.

With respect to specialized health management personal, more specialized information may be obtained. For example, a Senior Care Specialist may ascertain a caller's relationship to insured, identify the insured (or the insured's family's)

goals for the consultation, and obtain a brief history of the situation. This may include the insured's living situation, most pressing issues, immediate safety and medical concerns. With respect to potential use of long-term care benefits, the history may include any concerns of abuse or neglect, whether any dementia is present of suspected, the identity of the primary caregiver and the primary caregiver's employment and support system, any family dissention, financial concerns or other perceived barriers, the history of treatment or interventions tried and the assistance/services that are presently being received.

The determination of needs may occur through a discussion with a trained coach or specialist, or may follow a scripted set of areas or questions for examination, which may be maintained in a computer database to ensure that all required information and areas are covered. Following the determination of needs, the available resources through the HMP are examined, as illustrated by box C3. This may be conducted by the coach or specialist, or may be conducted by a computer executing commands contained as lines of software code, in accordance with a protocol and examining a database of available resources.

Once the resources have been examined, the action determined to be appropriate is taken by the HMP, as illustrated by box C4. This may be a referral to a community resource, outside professional, a counselor or a specialized health management professional by a coach, the revising of the personalized health management plan and the generation of a new periodic contact schedule or other available appropriate options. For example, should an insured by be concerned about weight management, or be diagnosed with diabetes or high blood pressure, contact with the HMP may be made and a coach may provide appropriate referrals and information. In this way, an insured may realize, at a younger age, an immediate benefit from a long-term care insurance policy, which allows for more flexible marketing of the policies and may encourage sales to younger individuals interested in health management plans.

For specialized health management personnel, appropriate action may include the education of the insured or the insured's caregiver on relevant aspects of the care receiver's situation and condition (as allowed by HIPAA or other law). It may also include providing information on possible and cost-effective resources, alternatives and solutions, making appropriate referrals to categories of medical professionals such as gerontologists, mental health services, specialists, rehabilitation therapies, balance centers, home safety assessment, adaptive equipment, PERS, hospice, etc., making appropriate referrals to financial services such as Medicaid qualification, accountants, etc., and advising the insured to assist in determining suitability. Where appropriate, actions such as making referrals to legal services such as elder law attorneys, estate-planning attorneys, Office of Public Guardian, Adult Protective Services, etc., making appropriate referrals to Aging Services programs such as Meals on Wheels, Senior Centers, National Family Caregiver Support Program, Medicaid waiver programs, subsidized housing, transportation services, Medicare/Medicaid questions, etc., and making appropriate resources to community resources such as the Alzheimer's Association, support groups, adult day programs, respite care, faith communities, hiring a private caregiver, etc., may be taken. Appropriate counseling in long-term care placement decisions and education on the available options may be provided by a Senior Care Specialist. Additionally, a Senior Care Specialist may assist the insured and the caregiver in identifying their informal support systems of family, friends, neighbors, and church resources. The need for follow-up with should be ascertained and, if needed scheduled.

The appropriate action to be taken may be determined by the comparison of the data obtained against the known averages fro the relevant populations, as discussed previously herein. Where the insured is within a "normal" range with respect to a specific health area, continuation of the health management services may be all that is required. Where the insured is categorized as "at risk" to a category, a more intensive intervention may be undertaken. The purpose of the more intensive intervention may be to extend the ability of the insured to maintain an independent lifestyle and not require long-term care. Such an intensive intervention may include in-person coaching, frequent contacts to discuss or provide training and support for specific issues and referrals to appropriate health care personnel.

Where desirable, a consultation on long-term care should be provided for each insured, before long-term care benefits are utilized. This allows the insured or the insured's caregiver or family to receive assistance in selecting appropriate long-term care. A consultation as outlined in the proceeding paragraph should be provided with the information outlined above gathered from, and provided to the insured, as appropriate. At this time, unless otherwise covered in the consultation, a Senior Care Specialist should also offer other information as appropriate. Examples of such information may include information on: 1) important legal documents for seniors: advance directive, will, durable powers of attorney for finances and health care, 2) Alzheimer's Disease, 3) Prescription drug assistance programs, 3) Aging Services, 4) National Family Caregiver Support Services, 5) Adaptive Equipment, and any other suitable information. Assistance in providing suitable long-term care and information on the various options should also be provided.

Where insureds go "off-benefit" and are no longer using the long-term care benefits of the insurance policy, appropriate action may include providing the insured with an "action pal" detailing actions and support that are needed for continued improvement of conditions or maintenance of health. For example, where an insured utilizes the long term care policy to cover care for a condition (such as recuperative care following major surgery) and no longer requires that policy benefit (at the end of such care), an "action plan" detailing action to firther improve that condition ant to otherwise maintain health status may be provided. Such action plans may be prepared in conjunction with the appropriate health care providers.

Where appropriate and allowed under the law, the HMP may provide information gathered regarding the insured during the provision of the personalized health management plan to the insurer for use in underwriting, reflected in rate adjustments over time, or for the revision of underwriting rules and assumptions for prospective insureds based upon the experiences of actual insureds. It will be appreciated that the HMP may be a division or operating unit of an insurance company offering policies that operates in accordance with the methods of the present invention, or may be a separate entity that offers health and benefit management services and contracts with an insurer to provide health management services in connection with a long-term care policy.

While this invention has been described in certain embodiments, the present invention can be further modified with the spirit and scope of this disclosure. This application is therefore intended to cover any variations, uses, or adaptations of the invention using its general principles. Further, this application is intended to cover such departures from the present disclosure as come within known or customary practices in the art to which this invention pertains and which fall within the limits of the appended claims.

What is claimed is:

1. A method for offering, by an insurer, long-term care insurance with personalized health management health benefits provided to an insured prior to a need for utilization of benefits of the long-term care insurance, the method comprising:

the insurer conducting a health status examination of a potential insured, wherein the health status examination comprises a health status assessment;

the insurer generating a personal health report of the potential insured based upon the health status assessment, wherein generating a personal health report comprises utilizing a computer having a processor and following commands contained in software executing commands contained as lines of software code, in accordance with a protocol and examining a database of available resources;

the insurer offering a long-term care insurance policy providing health management health benefits to the potential insured at an insurance rate;

the potential insured purchasing the long-term care insurance policy so as to become an insured;

inputting, into the computer, data relating to the results of the health status assessment of the insured, which is then automatically routed in a communication to a health management provider as a document in paper form, in a computer readable format contained on computer readable media, or as a data transmission, said health management provider being a separate entity than the insurer;

the health management provider developing a personalized health management plan for the insured based upon results of the health status assessment conducted by the insurer and generated by the computer;

the health management provider providing personalized health management services to the insured based upon the personalized health management plan generated by the computer.

2. The method according to claim 1, further comprising generating a personal health report based on the results of the health status examination.

3. The method according to claim 2, further comprising providing a copy of the personal health report to the potential insured.

4. The method according to claim 1, wherein the provision by the health management provider of personalized health management services to the insured comprises scheduling periodic contacts with the insured, based upon predicted health management needs based on the health status assessment of the insured and providing information concerning predicted health care issues.

5. The method according to claim 4, further comprising revising predicted health management needs of the insured based upon information obtained during the periodic scheduled contacts by the health management provider of the insured.

6. The method according to claim 4, wherein providing information to the insured concerning predicted health care issues by the health management provider comprises the health management provider providing information to the insured related to arthritis, asthma, cancer, chronic obstructive pulmonary disease, heart disease, depression or anxiety, diabetes, high blood pressure, stroke risks, obesity and weight management or osteoporosis.

7. The method according to claim 4, wherein providing information concerning predicted health care issues comprises referring the insured to a therapist for mental health counseling.

8. The method according to claim 1, wherein providing personalized health management services to the insured comprises the health management provider scheduling periodic contacts with the insured, based upon predicted health management needs for providing referrals to services for anticipated health care needs of the insured in view of the health status examination.

9. The method according to claim 1, wherein developing a personalized health management plan for the insured based upon the results of the health status examination comprises comparing numerical values representing the status of the potential insured in various health issues that are obtained from the insured to known averages for those numerical values for a given relevant population of individuals.

10. The method according to claim 9, wherein developing a personalized health management plan for the insured based upon results of the health status examination comprises classifying the insured into a risk group based upon the deviance of a numerical value for the insured from an average for the given relevant population of individuals.

11. The method according to claim 1, wherein providing personalized health management services by the health management provider to the insured comprises the health management provider responding to contacts initiated by the insured to provide information for health management issues.

12. The method according to claim 1, wherein providing personalized health management services to the insured comprises referring the insured to a Senior Care Specialist for assistance with selecting and obtaining long-term health care.

13. The method according to claim 12, wherein providing personalized health management services by the health management provider to the insured further comprises having the Senior Care Specialist provide information on important legal documents for seniors, Alzheimer's Disease, prescription drug assistance programs, Aging Services, National Family Caregiver Support Services, and Adaptive Equipment to a caregiver of the insured.

14. The method according to claim 1, wherein the insurer stratifying the risk of providing long-term care insurance to the potential insured based upon results of the health status examination comprises the insurer assigning the potential insured to a risk group based upon the results of the health status examination of the potential insured.

15. The method according to claim 1, wherein the health status assessment comprises administration by the insurer of an SF-36® health survey.

16. The method according to claim 1, wherein conducting a health status examination with a potential insured comprises administering the health status assessment by a personal interview, a medical exam or by computer-based questioning.

17. A system for providing a personalized health management plan and health management services to an insured individual under a long-term care insurance policy offering long-term care benefits, prior to a need of the insured individual for utilization of the long-term care benefits, the system comprising:

a computer having a processor and following commands contained in software executing commands contained as lines of software code, in accordance with a protocol and examining a database of available resources, wherein the software is operatively configured to enable:

an insurer to provide long-term care benefits to the insured individual under a long-term care insurance policy;

a separate health management provider to communicate with the insurer concerning the insured individual; and the separate health management provider to provide a personalized health management plan and health management services to the insured individual based upon the communications with the insurer;

the communications with the insurer to comprise a communication selected from the group consisting of a document in paper form, a computer readable format contained on computer readable media, and a data transmission; and the separate health management provider to prepare, under the long-term care insurance policy provided by the insurer, a personalized health management plan for the insured individual, which is generated by the computer prior to the need for utilization of long-term care benefits of the long-term care insurance by the insured individual.

18. The system of claim 17, wherein the health management provider comprises an entity that schedules periodic contacts with the insured individual, based upon predicted health management needs based on a personal health status assessment of the insured individual and provides information to the insured individual concerning predicted health care issues or refers insured the individual to services for anticipated health care needs of the insured individual.

19. A method for offering, by an insurer, an insurance policy consisting of long-term care insurance together with personalized health management health benefits provided to an insured prior to a need for utilization of benefits of the long-term care insurance, the method comprising:

the insurer conducting a health status examination of a potential insured, wherein the health status examination comprises a health status assessment;

the insurer generating a personal health report of the potential insured based upon the health status assessment, wherein generating a personal health report comprises utilizing a computer having a processor and following commands contained in software executing commands contained as lines of software code, in accordance with a protocol and examining a database of available resources;

the insurer offering a long-term care insurance policy providing health management health benefits to the potential insured at an insurance rate;

the potential insured purchasing the long-term care insurance policy so as to become an insured;

inputting, into the computer, data relating to the results of the health status assessment of the insured, which is then automatically routed in a communication to a health management provider as a document in paper form, in a computer readable format contained on computer readable media, or as a data transmission, said health management provider being a separate entity than the insurer;

the health management provider developing a personalized health management plan for the insured based upon results of the health status assessment conducted by the insurer and generated by the computer;

the health management provider providing personalized health management services to the insured based upon the personalized health management plan generated by the computer.

20. A method for offering, by an insurer, an insurance policy consisting of long-term care insurance together with personalized health management health benefits provided to an insured prior to a need for utilization of benefits of the long-term care insurance, the method comprising:

the insurer conducting a health status examination of a potential insured, wherein the health status examination comprises a health status assessment;

the insurer generating a personal health report of the potential insured based upon the health status assessment, wherein generating a personal health report comprises utilizing a computer having a processor and following commands contained in software executing commands contained as lines of software code, in accordance with a protocol and examining a database of available resources;

wherein the personal health report is a visual representation of the health status of the potential insured depicted by the computer;

the insurer offering a long-term care insurance policy providing health management health benefits to the potential insured at an insurance rate;

the potential insured purchasing the long-term care insurance policy so as to become an insured;

inputting, into the computer, data relating to the results of the health status assessment of the insured, which is then automatically routed in a communication to a health management provider as a document in paper form, in a computer readable format contained on computer readable media, or as a data transmission, said health management provider being a separate entity than the insurer;

the health management provider developing a personalized health management plan for the insured based upon results of the health status assessment conducted by the insurer and generated by the computer; and the health management provider providing personalized health management services to the insured based upon the personalized health management plan generated by the computer.

* * * * *